(12) United States Patent
Kräutler et al.

(10) Patent No.: US 8,008,339 B2
(45) Date of Patent: Aug. 30, 2011

(54) NON-FLUORESCENT CHLOROPHYLL CATABOLITES

(75) Inventors: Bernhard Kräutler, Innsbruck (AT); Thomas Müller, Innsbruck (AT)

(73) Assignee: Leopold-Franzens-Universitat Innsbruck, Innsbruck (AT)

( * ) Notice: Subject to any disclaimer, the term of this patent is extended or adjusted under 35 U.S.C. 154(b) by 196 days.

(21) Appl. No.: 12/073,888

(22) Filed: Mar. 11, 2008

(65) Prior Publication Data
US 2008/0227842 A1 Sep. 18, 2008

Related U.S. Application Data

(63) Continuation of application No. PCT/AT2006/000370, filed on Sep. 6, 2006.

(30) Foreign Application Priority Data

Sep. 12, 2005 (AT) .................... A 1488/2005

(51) Int. Cl.
*A61K 31/40* (2006.01)
*C07D 411/00* (2006.01)
(52) U.S. Cl. ......... 514/414; 548/466; 548/467; 548/468
(58) Field of Classification Search .................. 548/466, 548/467, 468; 514/414
See application file for complete search history.

(56) References Cited

U.S. PATENT DOCUMENTS
2003/0023081 A1 1/2003 Nifantiev et al.

OTHER PUBLICATIONS

MacDougall, Colour in Food Improving quality, Woodhed pub. ltd, pp. 218, 179, 262, 261, (2002).*
Krautler, The Pigments of Life 7th Schrodinger-Lecture, Trinity College Dublin, pp. 1-8, (2001).*
International Search Report (with English translation) issued Mar. 2, 2007 in the International (PCT) Application PCT/AT2006/000370 corresponding to the present U.S. application.
Austrian Search Report (with English translation) completed Jul. 24, 2006 in Austrian Application No. A 1488/2005 corresponding to the present U.S. application.
Joachim Berghold et al., "Chlorophyll Breakdown in Tobacco: On the Structure of Two Nonfluorescent Chlorophyll Catabolites", Chemistry and Biodiversity, vol. 1(4), pp. 657-668, 2004.
Michael Oberhuber et al., "Breakdown of chlorophyll: A nonenzymatic reaction accounts for the formation of the colorless 'nonfluorescent' chlorophyll catabolites", Proceedings of the National Academy of Sciences of the United States of America, vol. 100, No. 12, pp. 6910-6915, 2003.
Joachim Berghold et al., "Chlorophyll Breakdown in spinach: on the structure of five nonfluorescent chlorophyll catabolites", Photosynthesis Research, vol. 74(2), pp. 109-119, 2002.
Michael Oberhuber et al., "Chlorophyll Breakdown—On a Nonfluorescent Chlorophyll Catabolite from Spinach", Helvetica Chimica Acta, vol. 84(9), pp. 2615-2627, 2001.
Fosca Gattoni Losey et al., "Isolation and Characterization of a Urobilinogenoidic Chlorophyll Catabolite from *Hordeum vulgare* L.", Journal of Biological Chemistry, vol. 276, No. 12, pp. 8643-8647, 2001.
Christophe Curty et al., "Detection, Isolation and Structure Elucidation of a Chlorophyll α Catabolite from Autumnal Senescent Leaves of *Cercidiphyllum japonicum*", Phytochemistry, vol. 42, No. 6, pp. 1531-1536, 1996.
B. Kräutler, "Unravelling chlorophyll catabolism in higher plants", Biochemical Society Transactions, XP002420697, pp. 625-630, 2002.
Bernhard Kräutler, "Chlorophyll Breakdown and Chlorophyll Catabolites", The Porphyrin Handbook, vol. 13, pp. 183-209, 2003.
Walter Mühlecker et al., "Breakdown of chlorophyll: Constitution of nonfluorescing chlorophyll-catabolites from senescent cotyledons of the dicot rape[(1)]", Plant Physiology and Biochemistry, vol. 34(1), pp. 61-75, 1996.
Walter Mühlecker et al., "Breakdown of Chlorophyll: A Tetrapyrrolic Chlorophyll Catabolite from Senescent Rape Leaves", Helvetica Chimica Acta, vol. 76(8), pp. 2976-2980, 1993.
David E. Baranano et al., "Biliverdin reductase: A major physiologic cytoprotectant", PNAS, vol. 99, No. 25, pp. 16093-16098, 2002.
Manuela Zude-Sasse et al., "An approach to non-destructive apple fruit chlorophyll determination", Postharvest Biology and Technology, vol. 25, pp. 123-133, 2002.
Jose Iturraspe et al., "A New 5-Formylbilinone as the Major Chlorophyll α Catabolite in Tree Senescent Leaves", Journal of Organic Chemistry, vol. 60(21), pp. 6664-6665, 1995.

* cited by examiner

*Primary Examiner* — Janet L. Andres
*Assistant Examiner* — Raymond Covington
(74) *Attorney, Agent, or Firm* — Wenderoth, Lind & Ponack, LLP.

(57) ABSTRACT

The invention relates to a compound of formula (I), or a pharmacologically or cosmetically acceptable salt or derivative thereof, wherein $R_1$ to $R_5$ are selected from the groups $R_1$ representing -alkyl, -vinyl, —CHOH—$CH_2$OH, $R_2$ representing H, —OH, —Oalkyl, —Oacyl, saccharide groups, modified saccharide groups (e.g. malonylated), $R_3$ representing —H, —OH, —Oalkyl, —Oacyl, modified —Oacyl (e.g. malonylated), saccharide groups, modified saccharide groups (e.g. malonylated), $R_4$, $R_5$ representing —COOH, -carbonic esters, for use as drug, antioxidant, food supplement. The invention also relates to a method for producing the compound of formula (I).

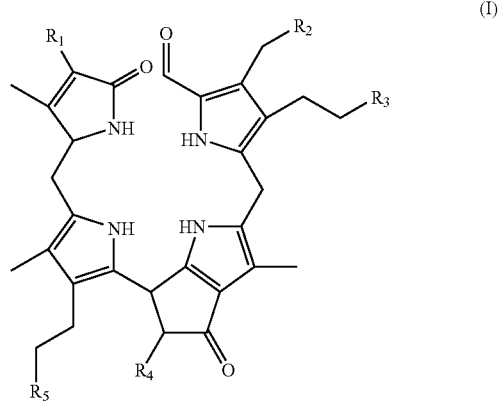

44 Claims, 10 Drawing Sheets

Figure 5A:
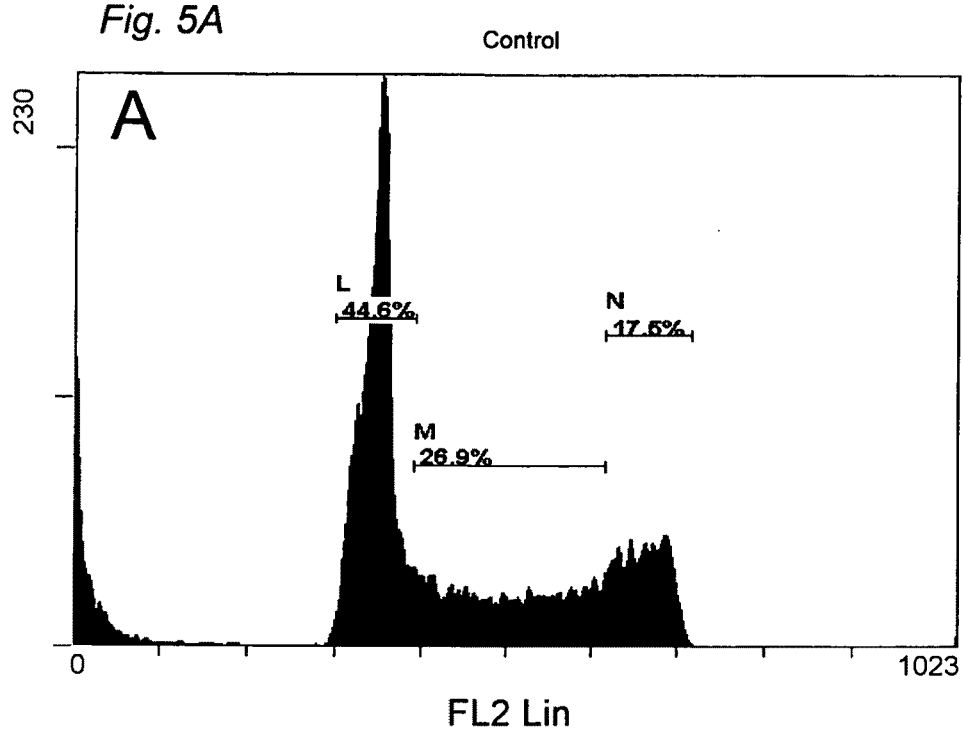
Figure 5D:
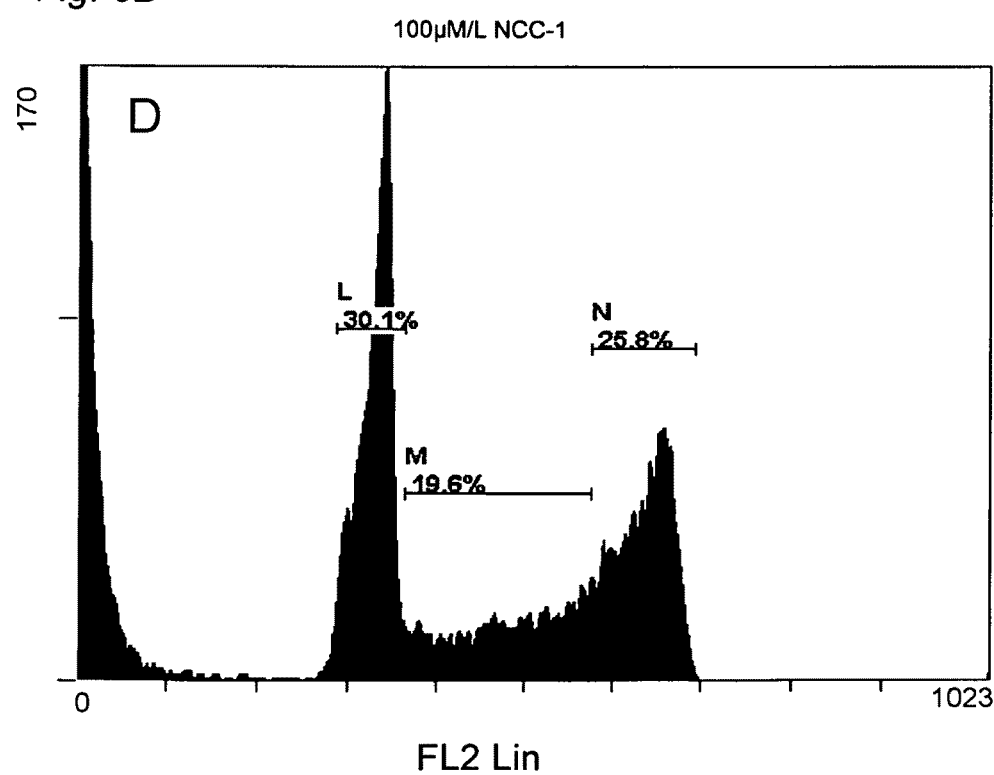
Figure 5C:
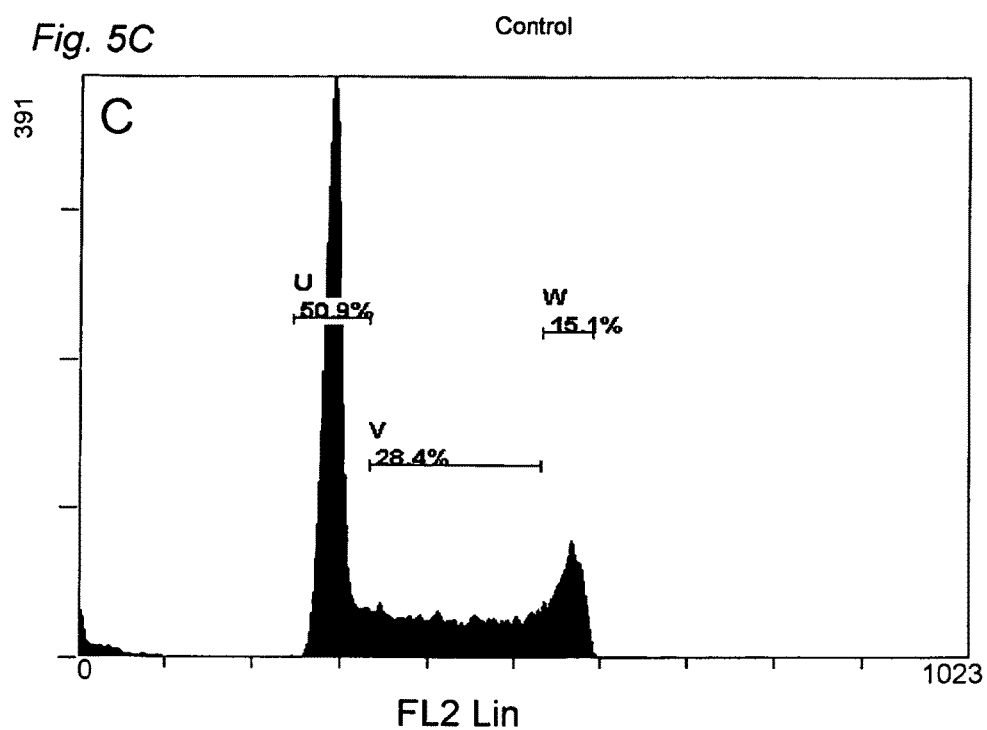
Figure 5F:
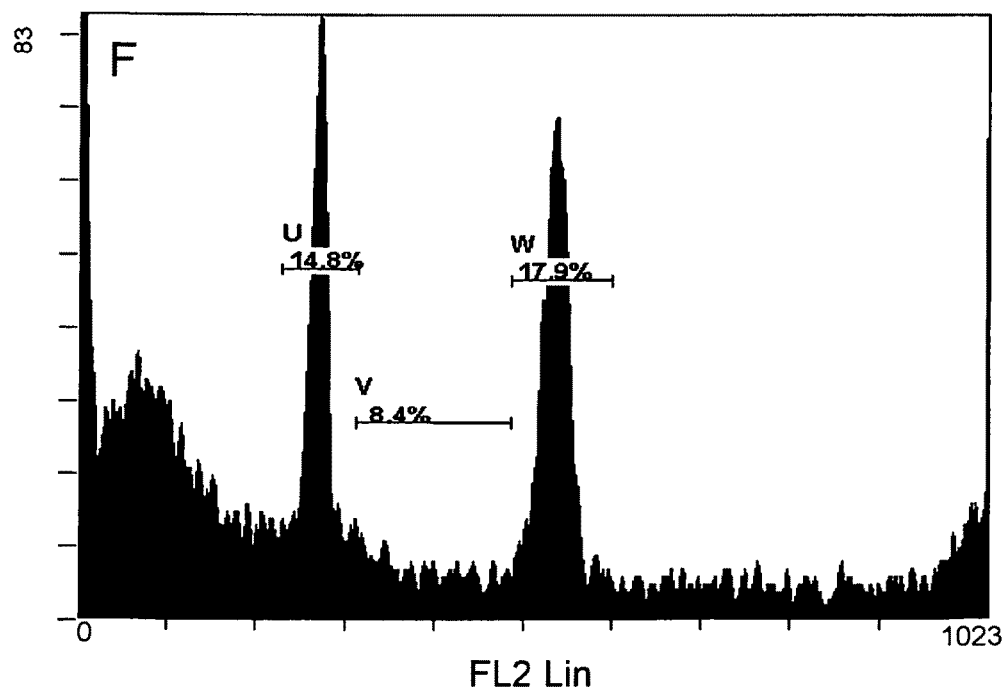

Fig. 5B  Control
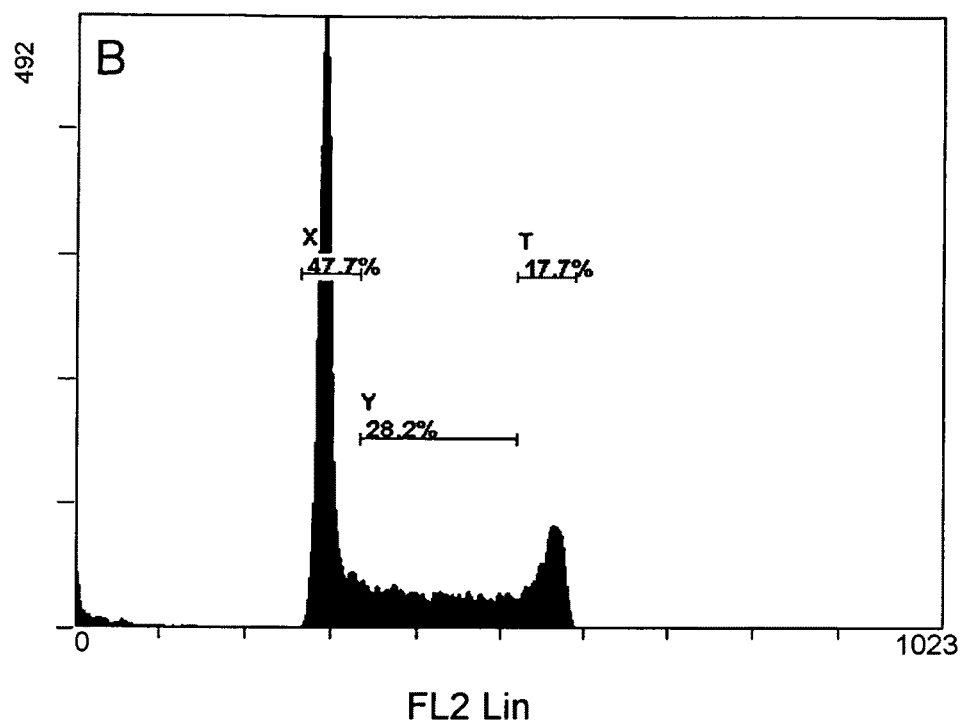
FL2 Lin
Fig. 5E  100μM/L NCC-1
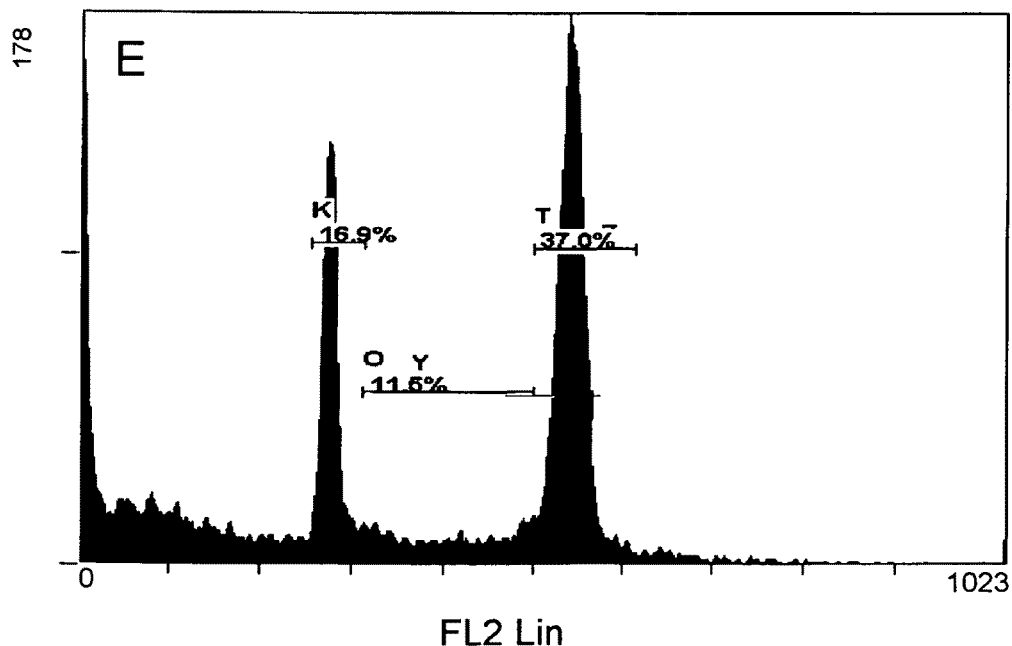
FL2 Lin

NON-FLUORESCENT CHLOROPHYLL CATABOLITES

This application is a continuation application of International application No. PCT/AT2006/000370, filed Sep. 6, 2006.

The invention relates to non-fluorescent chlorophyll catabolites (NCCs), their use and a process for producing such chlorophyll catabolites.

Chlorophyll breakdown is a seasonal event during which approximately $10^9$ tons of chlorophyll are broken down annually throughout the world. What actually happens to chlorophyll when the leaves turn yellow in the fall was unknown for a long time. It is only in the last two decades that chlorophyll has been successfully traced after the green color has disappeared [Kräutler, Bernhard. Chlorophyll Breakdown and Chlorophyll Catabolites. In: The Porphyrin Handbook. Kadish, K. M., Smith, K. M., Guilard R. (eds.), Elsevier Science 2003, Vol. 13, section 82, pp. 183-209]. If this complex process is compared to a puzzle, many important, but not yet all, parts of this puzzle have been successfully fitted together. What is currently known is that the so-called "non-fluorescent" chlorophyll catabolites, NCCs for short, which can be found in the vacuoles of aged plant cells, approximately twelve structurally slightly different NCCs of which are known to date which have been isolated from the leaves of various senescent plants, form the last link in this breakdown chain. However, very little is known about the functions of this type of compound.

The invention is based on the surprising finding that such NCCs are contained in ripe fruits, e.g. in apples and pears, in particular in the skins of such fruits, and are therefore also consumed. The finding that NCCs form a component of the human food chain indicates that NCCs firstly have no toxic properties and secondly represent an important component of human nutrition the effect of which is as yet unknown.

On the basis of this finding, which gives a whole new dimension to the significance of these compounds, the question arises whether this hitherto disregarded naturally occurring substance plays a specific part in our metabolism?

In most cases, the extraction and in particular the purification of these compounds is very costly. The senescent leaves of a tree called *Cerciphyllum Japonicum* represent a favorable source for the isolation of NCCs. In the case of this tree, which is called Judasblattbaum or Lebkuchenbaum in German, the chlorophyll is broken down into just two different compounds, for the most part into Cj-NCC-1 (always called NCC-1 below) [Oberhuber, M., Berghold, J., Breuker, K., Hörtensteiner, S., Kräutler, B. Breakdown of Chlorophyll: A Nonenzymatic Reaction Accounts For the Formation of The Colorless "Nonfluorescent" Chlorophyll Catabolites. Proc. Natl. Acad. Science U.S.A. (2003), Vol. 100, pp. 6910-6915]. The first isolation and characterization of Cj-NCC-1 was described by Curty and Engel in 1996 [Curty, C. and N. Engel. Detection, Isolation and Structure Elucidation of a Chlorophyll a Catabolite from Autumnal Senescent Leaves of *Cercidiphyllum Japonicum*, Phytochemistry (1996), Vol. 42, no. 6, pp. 1531-1536].

All processes hitherto published for isolating NCCs from plant materials are suitable only for producing these compounds on milligram scale (in the range from 1-20 mg NCC) for structure analysis (e.g. NMR, UV). The work steps are time- and labor-intensive and unsuitable for the isolation of substantial quantities of pure NCCs. This is above all due to the fact that with all these processes either preparative thin layer chromatography (TLC) or preparative HPLC are used and both processes make an upscaling impossible. In addition, experience shows that when isolating NCCs by means of preparative TLC an oxidative decomposition to form colored breakdown products cannot be prevented. As scientific interest has hitherto focused on the clarification of the structure of new chlorophyll catabolites, the production or isolation of substantial quantities has not been required.

The object of the invention is therefore the development of a novel process with which substantial quantities of NCCs can be produced easily with a much higher degree of purity than in the state of the art.

The process according to the invention for producing non-fluorescent chlorophyll catabolites with the chemical formula I

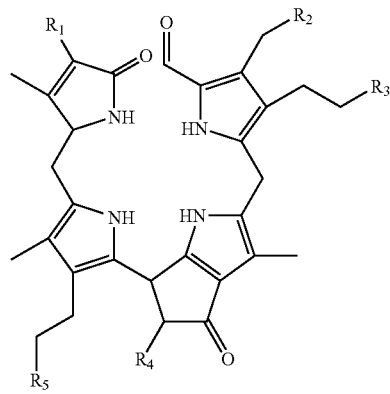

or a pharmacologically, dermatologically or cosmetically acceptable salt or derivative thereof, wherein $R_1$ to $R_5$ is selected from the radicals $R_1$-alkyl, -vinyl, —CHOH—$CH_2OH$ $R_2$—H, —OH, —Oalkyl, —Oacyl, saccharide radicals, modified saccharide radicals (e.g. malonylated)

$R_3$—H, —OH, —Oalkyl, —Oacyl, modified —Oacyl (e.g. malonylated), saccharide radicals, modified saccharide radicals (e.g. malonylated)

$R_4$, $R_5$—COOH, carboxylic acid ester and also its salts and solvates from plant material, in particular from plant leaves, is characterized by the steps:

extraction of the plant material with a first solvent or solvent mixture with a dielectric constant of 5 to 20 and a dipole moment of 5 to $10 \times 10^{-30}$ cm to form a crude extract filtration or chromatography of this extract over silica gel elution of the silica gel with a second solvent or solvent mixture, preferably with a greater dipole moment than the first solvent drawing off of the solvent and optional crystallization of the obtained residue.

It is possible to produce substantial quantities of NCCs of formula I with such a process.

It has proved particularly favorable to use $CH_2Cl_2$, methyl acetate, ethyl acetate, t-butanol, ethyl methyl ketone or mixtures thereof as first solvent. Methylene chloride is particularly suitable, but it has also been shown that methyl acetate and ethyl acetate are likewise very suitable solvents, wherein these two solvents are advantageously non-halogenated solvents, which improves the possibilities of future uses of the compound produced from such a process.

The extraction of the plant material with the first solvent results in a solution which also contains very many undesired components. In order to separate off substances which are also readily soluble in water, it has therefore proved advantageous if a purification step of the crude extract with a non-miscible solvent takes place before the filtration step.

It is also provided for the process according to the invention that the filtration step is carried out with a silica-gel-filled chromatography column. Such a filtration step over a chromatography column has the advantage that the conditions can be kept very constant (uniform throughflow, uniformly packed column) and standard equipment can be used.

In the case of the filtration step over silica gel, it has been shown if the dissolved extract is directly added that non-fluorescent chlorophyll catabolites adhere well to it while numerous other compounds which are dissolved in the first extract elute more quickly from the column. The elution step of the silica gel, i.e. the actual rinsing down of the NCC from silica gel, therefore advantageously takes place with a solvent which dissolves this class of compound again from the silica gel. It has proved favorable to use as second solvent a solvent which has a greater polarity than the first solvent and comes from the group acetone, ethyl methyl ketone, methanol, methanol-water mixtures, methyl acetate or mixtures thereof or from mixtures of the first solvents or solvent mixture with a solvent of greater polarity.

Even after the elution step of the silica gel, there are still some substances in the eluate which can be removed with an aqueous solution.

Once the solvent has evaporated in the last step, for example by a rotary evaporator, it has proved favorable if the residue from the evaporation step is crystallized and then filtered and dried. This clearly makes for a great increase in the life of NCCs, as unpurified NCCs decompose and change color very rapidly in air.

Moreover, it has also proved favorable for the filtration step if the silica gel has a particle size of less than 5000, preferably less than 1000.

It has furthermore proved advantageous to use as plant material plant parts which are green before senescence (ripening) because the chlorophyll quantity is naturally particularly large in the green plant components. It is particularly favorable if substantially senescent or ripened plant material is used as plant material because the chlorophyll has then already been at least partly catabolized to NCC. As NCCs decompose rapidly in harvested plants, it is advantageous to use as plant material freshly harvested, senescent or ripened plant material which has been stored at approximately −20° C. or below after the harvest. It has been shown that particularly large quantities of NCCs were obtained when the plant material comes from agricultural plants such as oil seed rape, clover, barley, corn, tobacco, from herbaceous plants and agriculturally produced vegetables such as spinach, broccoli, pepper, from shrubs and broad-leaved trees such as witch hazel, elms, sycamores, walnuts, *Cercidiphyllum japonicum* and from conifers such as larches.

The new process is characterized by simple methods and automatable work steps, which for the first time allows isolation in pure form and crystallization of the chemically labile (oxidation-sensitive) compounds. Upscaling trials with larger working and glass equipment have shown that the process is very suitable, using recyclable solvents (cost efficiency) and practically loss-free, for preparing large quantities of high-purity NCCs on the gram scale (and larger quantities).

The process described here allows a rapid, simple and easily upscalable isolation of high-purity NCCs from normal plant materials. There is as yet no known process which allows isolation in pure form of NCCs and crystallization of NCCs in large quantities.

Due to the rapid processing and procedure during decisive work steps, the disruptive formation of structurally related, colored decomposition products can be completely suppressed for the first time.

The crystallization, as last work step, ensures maximum purity of the isolated compounds.

Halogenated hydrocarbons (such as dichloromethane or chloroform) are simultaneously solvents for the extraction and chromatography, and are easily recyclable.

But halogenated solvents can also be replaced by chlorine-free ethyl acetate or methyl acetate.

Senescent leaves (e.g. those of the tree *Cercidiphyllum japonicum*) are a very cheap, and (almost) inexhaustible source of NCCs (e.g. NCC-1). We also recently found the same sort of NCCs in fruits. But the fruits themselves are not suitable for the isolation of substantial quantities of NCCs because the latter were detectable only in very small quantities there.

Example of the Preparation of NCC-1 from Senescent Leaves of *Cercidiphyllum japonicum*:

1 kg cold leaf material (leaves from the Botanical Garden of Innsbruck University, Austria, gathered on 23 Oct. 2003, color: yellow-green, stored in the freezer at −80° C.) was mixed finely for 5 min (Braun Vario 600 W) in two batches of 0.5 kg each in a 5-l steel container with 1.4-l cold (5° C.) methylene chloride and 25 g ascorbic acid and filtered over a 1-cm cellite filter (diameter 14 cm). The filter cake was mixed twice more with 0.7 l cold methylene chloride each time, refiltered and rewashed with 100 ml cold methylene chloride.

The obtained clear solution (dark-green) was then transferred into a separating funnel and extracted with 1.5 l potassium phosphate buffer (c=100 mM, pH=5.2; 1 g ascorbic acid was added to 1 l buffer). The organic phase was drained over dried cotton wool (2 days in the drying cupboard at 100° C.) into a 3-l Erlenmeyer flask. The aqueous phase was reextracted with 200 ml and 100 ml methylene chloride and the methylene chloride phase likewise filtered off over dried cotton wool. The cotton wool was then rewashed with 100 ml methylene chloride. The two thus-obtained extracts (from 0.5 kg starting material each) were combined, cooled and added to the prepared chromatography column.

Column for the chromatography was prepared as follows:
column height: <=60 cm; column diameter: >=7 cm
silica gel layer: <=38 cm; beach sand layer: 0.5 cm
mobile solvent for column packing: 100% dist. methylene chloride The empty chromatography column was charged with 500 ml mobile solvent and the air removed under the fritted-glass filter by means of a hand pump. 300-700 g silica gel 60 was degassed in the ultrasound bath with 1.5 l dist. methylene chloride and packed into the column. The mobile solvent was drained accompanied by constant tapping to 3 cm above the silica gel layer. 0.5 cm beach sand was then added and the column cooled in the cold-storage room. The chromatography was carried out at approximately 4 degrees in the cold-storage room.

Mobile Solvents Used:
Mobile solvent mixture 1: 95% dist. methylene chloride, 5% dist. methanol (5 l in total)
Mobile solvent mixture 2: 90% dist. methylene chloride, 10% dist. methanol (2.5 l in total)

The addition of the extract to the column took approx. 1-3 h. The reaction mixture was then washed with 100 ml pure dist. methylene chloride, with the result that the residue above the sand was colorless. The column was then filled with mobile solvent mixture 1 (mixture of 95% dist. methylene chloride, 5% dist. methanol). Once the chlorophyll had been eluted (dark-green fractions), fractions of approx. 200 ml each were removed and analyzed by DC (Polygramm SIL G/UV 254 layer thickness 0.2 mm silica gel with fluorescent indicator, solvent: chloroform:methanol:water=95:10:1; with the reference substance Cj-NCC-1). After the first pure NCC-1 fraction (DC control), the mobile solvent was changed to mobile solvent mixture 2 (90% dist. methylene chloride, 10% dist. methanol). Fractions were collected until NCC-1 no longer trickled down from the column (DC control). Those fractions (2150 ml in total) which contained pure NCC-1 according to DC were combined in a separating funnel and extracted with 1 l potassium phosphate buffer (c=100 mM, pH=5.2/+1 g ascorbic acid on 1 l buffer). The org. phase was drained into a 3-lit. Erlenmeyer flask and the aqueous phase reextracted with 200 ml dist. methylene chloride. The org. phases were combined in the 3-l Erlenmeyer flask and filtered over dried cotton wool into two 2-l round-bottomed flasks. The cotton wool was rewashed with approx. 100 ml dist. methylene chloride. The light-yellow filtrate was then concentrated to approx. 100 ml on the rotary evaporator (25° C. bath temperature, p=400 mbar, with protection from light!), transferred into a 250-ml round-bottomed flask and evaporated again to dryness on the rotary evaporator.

The residue was dissolved in 5 ml dist. methylene chloride (basic-filtered over aluminum oxide) and filled to the brim with n-hexane (purum) in the 250-ml round-bottomed flask, wherein the NCC-1 precipitated out as a fine yellowish-white precipitate.

Isolation in Pure Form and Characterization

The contents of the round-bottomed flask were filtered off over a filter-paper disk (5 cm) and the residue transferred to a pill glass. The product was pre-dried for 15 min. on the rotary evaporator and then dried for 3 h under high vacuum.

Yield: 491 mg NCC-1 (as finely crystalline powder)

The obtained product was characterized by means of DC and UV.

The obtained product can be obtained with a degree of purity of 95%, preferably above 99%, particularly preferably above 99.5% (percentages by weight). NCC-1 is characterized in that $R_1$=-vinyl, $R_2$=—H, $R_3$=—OH, $R_4$=—COOCH$_3$, and $R_5$=—COOH.

It was surprising to find that an NCC which is identical to the relatively easily accessible NCC-1 from the Judas tree is found in apples (*Malus sylvestris*) or pears (*Pyrus communis*). This also showed us how to test in practice the chemical properties or biological importance of a hitherto disregarded component of food with diverse experiments. A "Golden Delicious" apple (with a diameter of approx. 8-10 cm) can, due to the quantity of chlorophyll present (according to Zude-Sasse, M., Truppel, I. and B. Herold. An approach to nondestructive apple fruit chlorophyll determination. Postharvest Biology and Technology 25 (2002), 123-133), contain at most approx. 0.1-1 mg NCCs.

Further details and advantages of the inventions and also embodiment examples are explained in more detail with reference to the figures and descriptions of the figures in the following statements.

There are shown in

Figure 1:
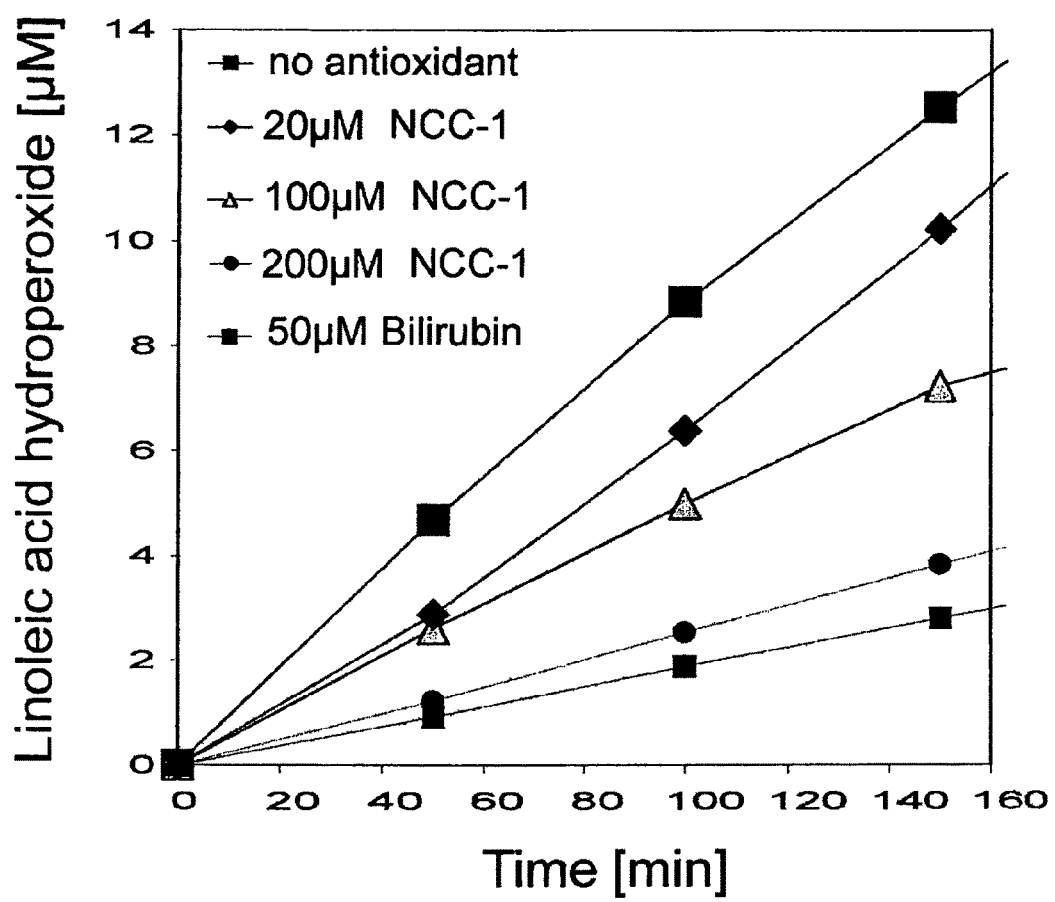
Figure 2:
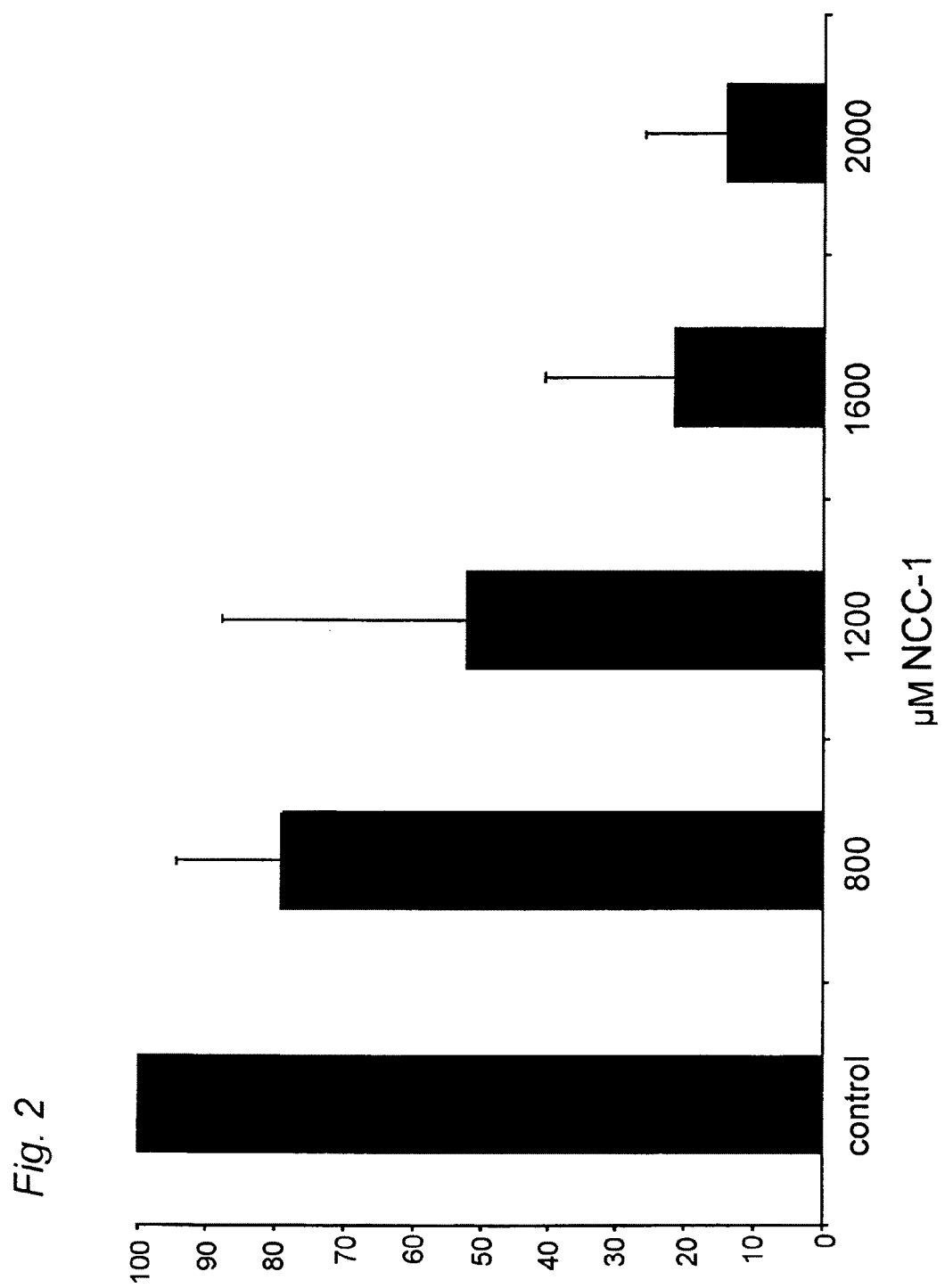
Figure 3A:
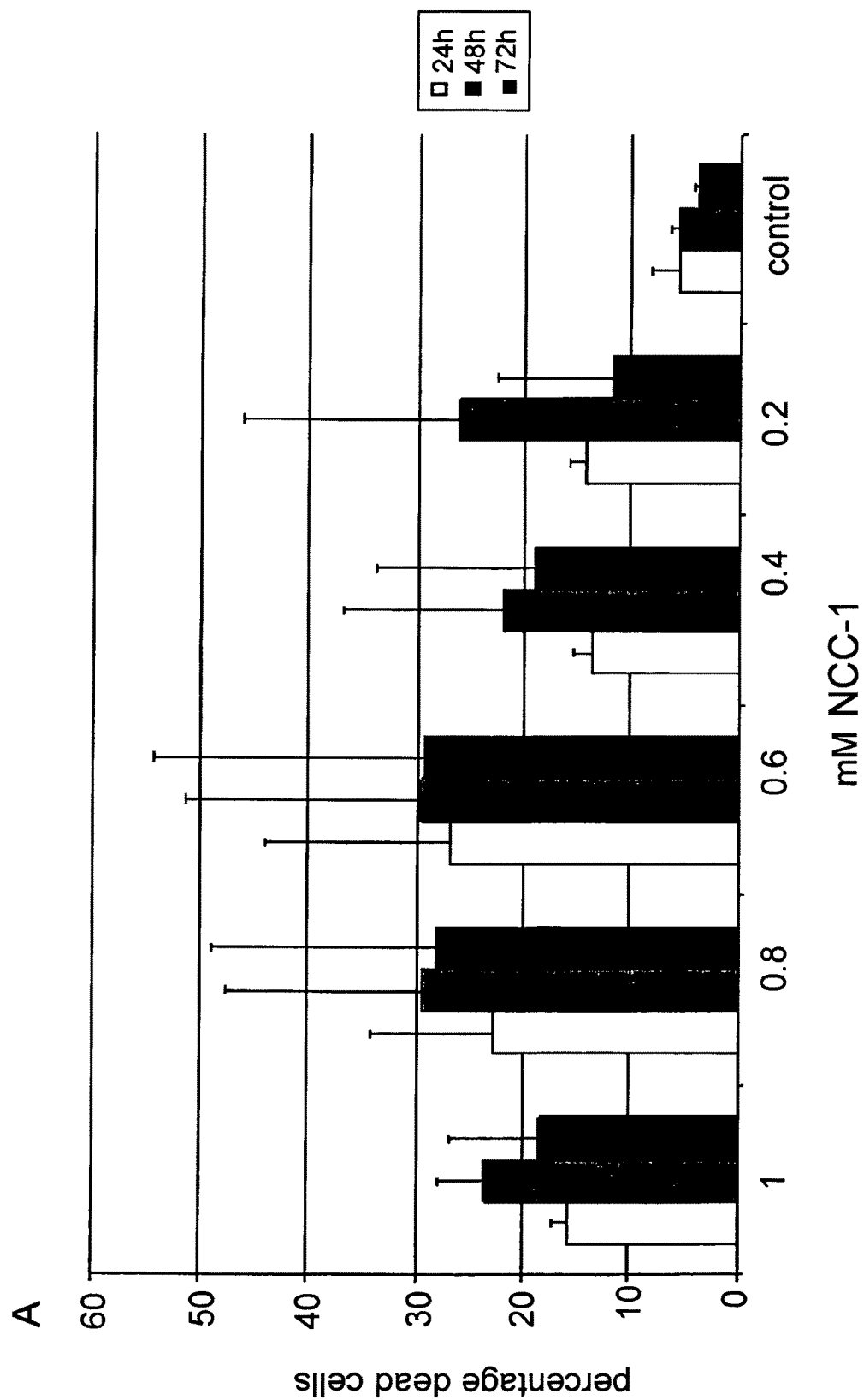
Figure 3B:
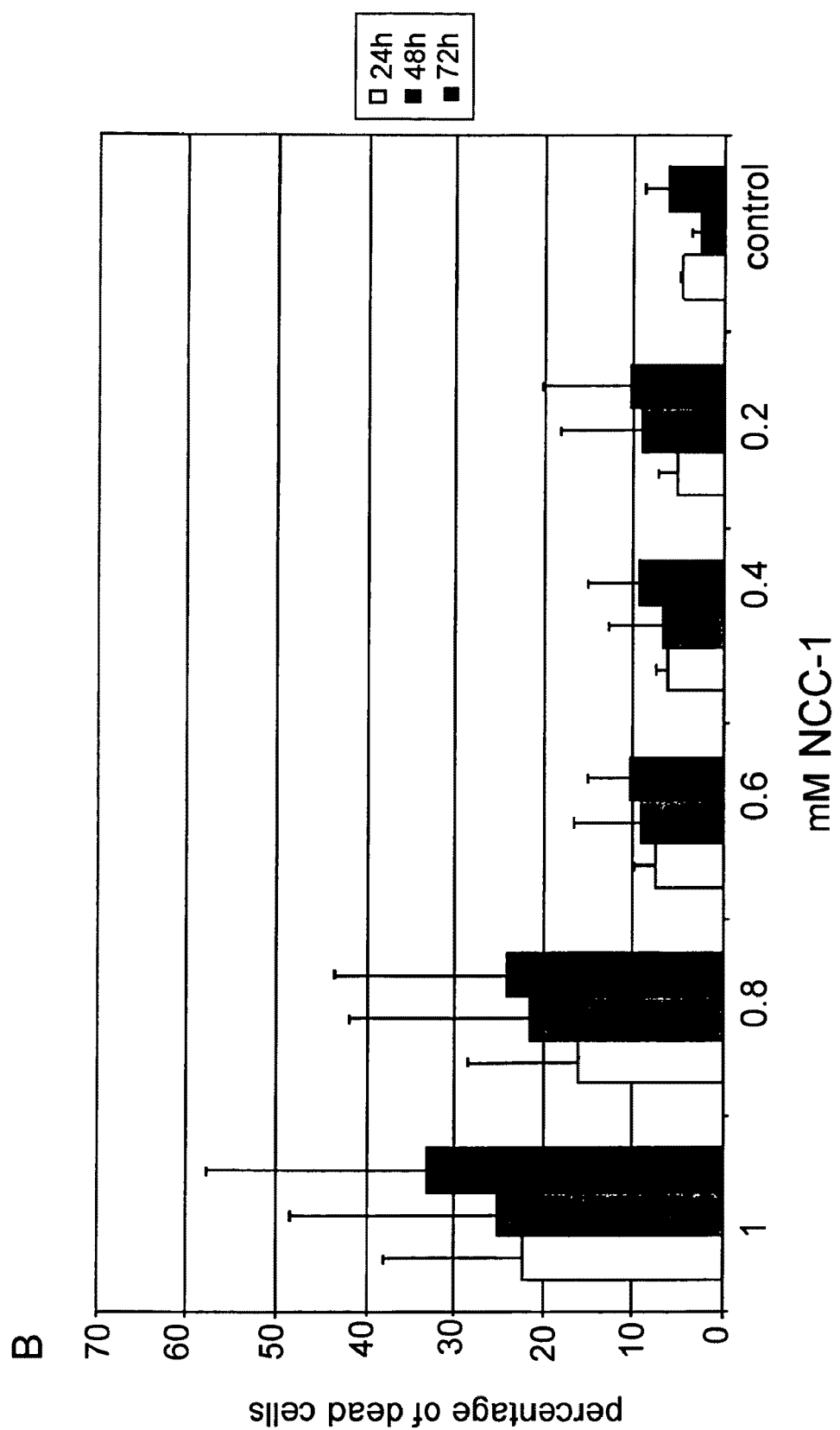
Figure 3C:
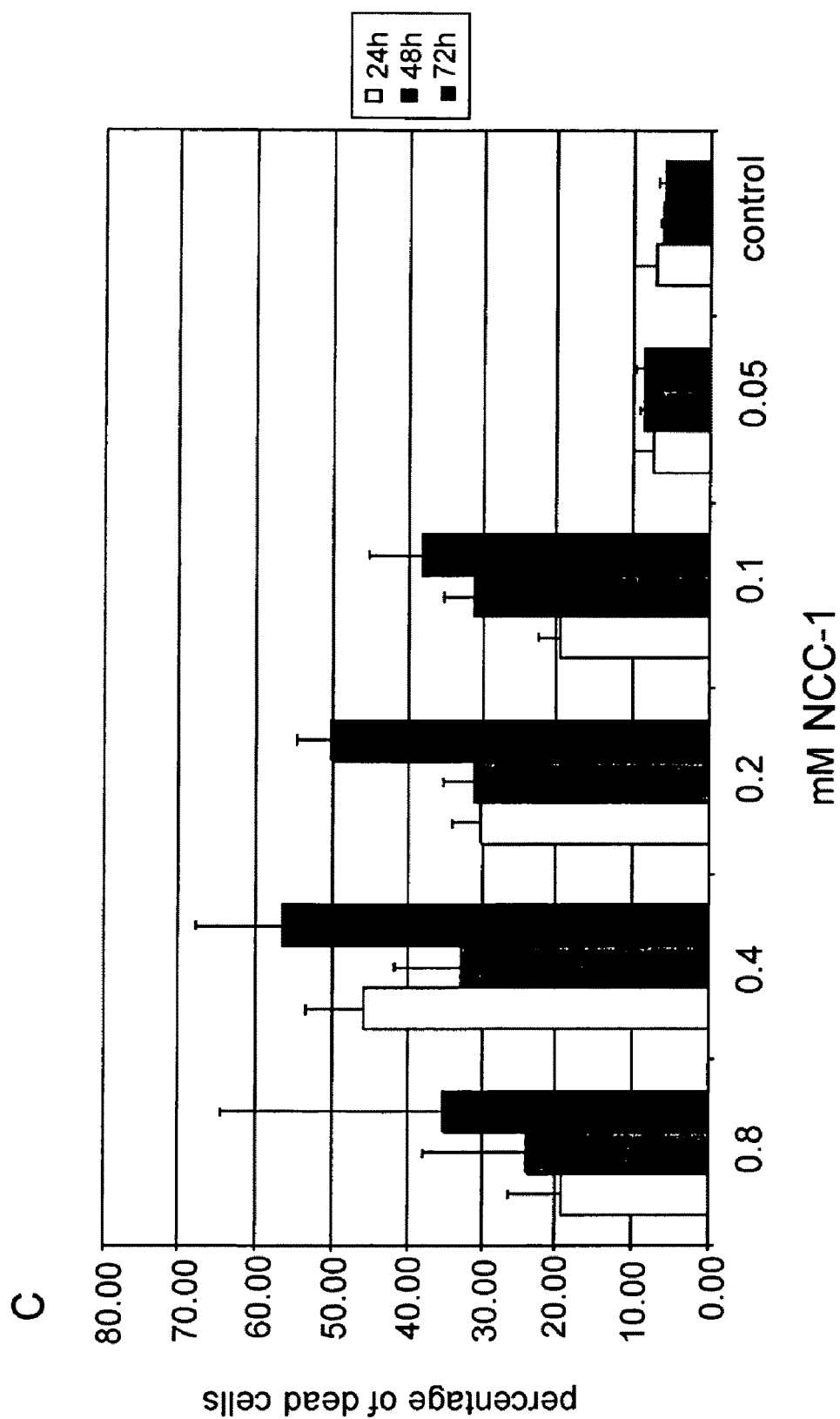
Figure 4:
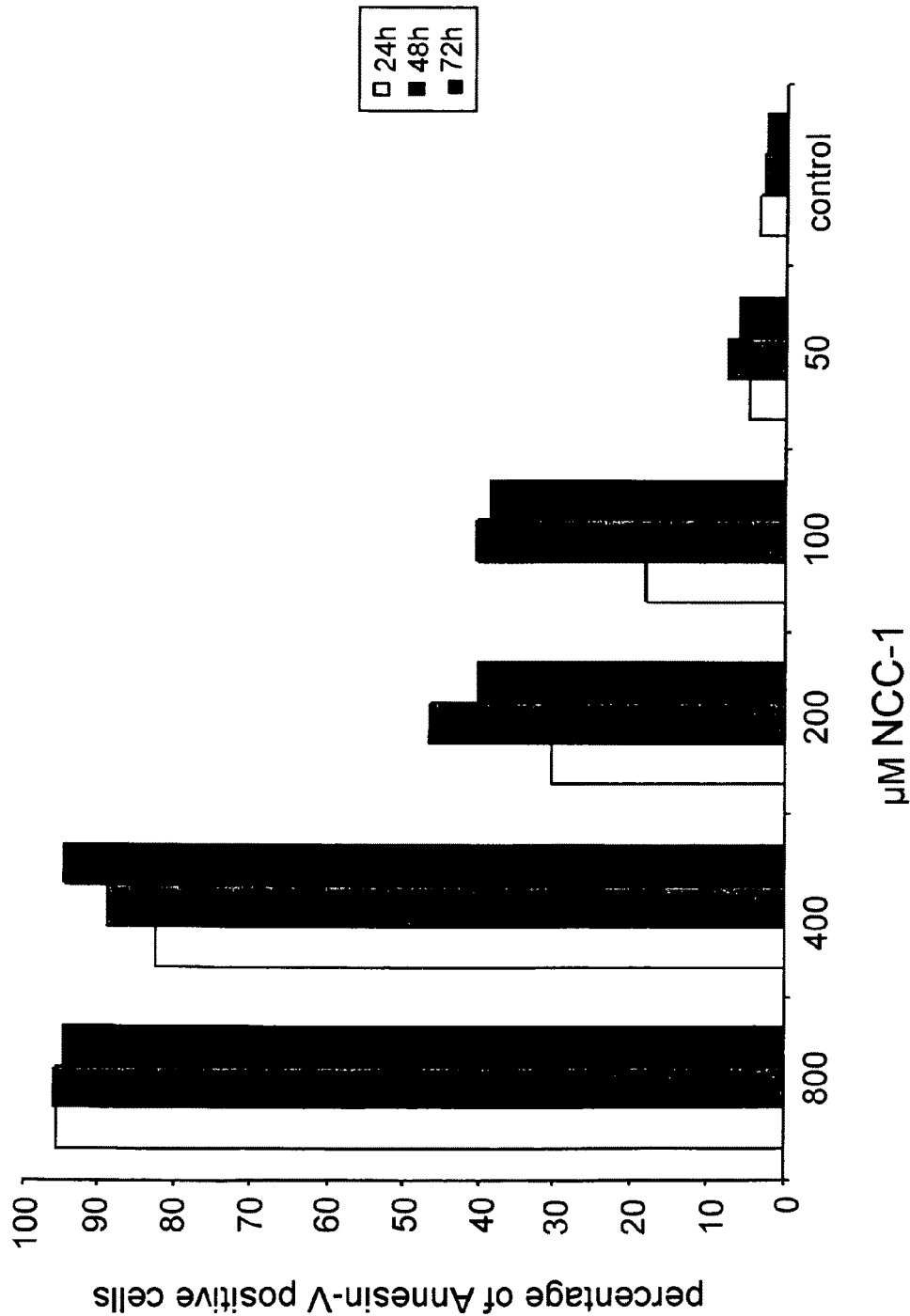
Figure 6:
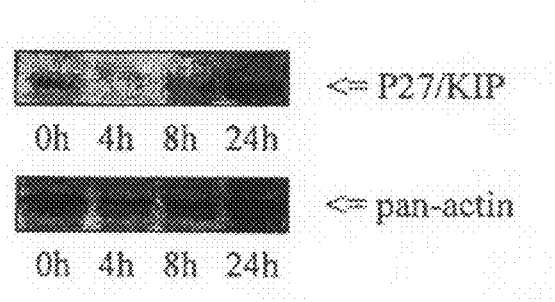

FIG. 1 tests to quantify the anti-oxidative action of bilirubin or NCC-1,

FIG. 2 the effect of NCC-1 on the growth of breast cancer cells of the MDAMB231 line, FIGS. 3A to 3C the induction of cell death in various cancer cell types, analyzed by means of flow cytometry, FIG. 4 the effect of NCC-1 on apoptosis in CCRF-CEM cells analyzed by means of flow cytometry, FIGS. 5A to 5F the effect of NCC-1-treatment on the cell cycle in CCRF-CEM cells, and FIG. 6 the effect of NCC-1 on the protein expression of p27/KIP in CCRF-CEM cells (Western blot).

It has been known for some time (e.g. in thin-layer chromatography) that NCCs decompose rapidly in air on silica gel (and in daylight) into rust-colored products, wherein an oxidation is presumed to be a feature for the decomposition. According to purification processes known hitherto only NCCs which were contaminated by decomposition products, and decomposed within several hours when stored, were ever able to be obtained. On the basis of this fact, it was known or to be assumed that under standard conditions (i.e. at room temperature and in the presence of atmospheric oxygen) NCC crude isolates are too unstable to have a targeted use. In a first surprising finding, it was now shown that NCCs have an antioxidative action under physiological conditions (in solution, organic or biological matrix; see below). On the basis of this surprising finding, more intensive tests on the antioxidative action of NCCs were carried out. The finding that crystallized NCCs in purified form, as they are obtained with the process according to the invention, keep well (can be stored almost undecomposed) when cooled despite the presence of oxygen, makes possible for the first time a targeted use of representatives of this class of compound.

As there is a certain chemical and biological relationship between heme catabolites (such as bilirubin) and chlorophyll catabolites (the NCCs), it was particularly interesting to examine the antioxidative effectiveness of NCCs, which was to be demonstrated using already established experiments by Stocker et. al. relating to the action of bilirubin [Stocker, R., Yamamoto, Y., McDonagh, A. F., Glazer, A., Arnes, B. N. Bilirubin Is an Antioxidant of Possible Physiological Importance. Science (1987), Vol. 235, pp. 1043-1046].

Both chlorophyll and heme belong to the class of the so-called porphyrinoid naturally occurring substances. Heme is a tetrapyrrolic ring system which as hemoglobin can transport oxygen in animal organisms with the help of a complexed iron atom. Central structure elements of a chlorophyll molecule are likewise a tetrapyrrolic ring system and a complexed magnesium atom which is capable of absorbing light energy in a controlled way in plant chloroplasts. Both plant and animal organisms have found ways as they have evolved to decompose these natural compounds under specific conditions in a targeted and controlled manner to form linear tetrapyrroles or excrete them.

While the breakdown products of chlorophyll are stored as non-fluorescent chlorophyll catabolites (NCCs) in the plant vacuole, the decomposed heme can be excreted via the kidneys in the form of bilirubin conjugate. In the case of animal organisms, the importance of the so-called biliverdin reductase, an enzyme which reduces biliverdin to bilirubin, which has a toxic action in larger concentrations, has long been a mystery. But in 2002 it was shown that the biliverdin-bilirubin redox cycle plays an important part in the protection of cells against oxidative stress [Baranano, D. E., Rao, M., Ferris, C. D., Snyder, S. H., Biliverdin Reductase: A Major Physiologic Cycloprotectant. PNAS (2002), Vol. 99, No. 25, pp. 16093-16098]. The antioxidative action of bilirubin, already known since 1987 [Stocker, R., Yamamoto, Y., McDonagh, A. F., Glazer, A., Arnes, B. N. Bilirubin Is an Antioxidant of Possible Physiological Importance. Science (1987), Vol. 235, pp. 1043-1046.] plays an essential part in this.

Stocker et. al. used a simple test system to quantify the antioxidative action of the heme decomposition product bilirubin. The essential fatty acid linoleic acid, a diunsaturated fatty acid, is very sensitive to an oxidation by free radicals. Such oxidations can cause extensive damage in the form of chain reactions e.g. in cell membranes. This "oxidative stress" has been simulated in vitro by the use of an azo compound (radical starter). By splitting off nitrogen ($N_2$), such azo compounds constantly form, independently of the temperature, carbon radicals which can in turn react with the unsaturated bonds of the fatty acids. Fatty acid radicals form which in turn react with oxygen. This leads to the formation of fatty acid hydroperoxides which are detectable by spectroscopy on account of their particular absorption properties in the UV region (234 nm). Depending on the concentration of the radical former, the number of fatty acid hydroperoxide molecules thus increases over time. If an active substance with an antioxidative action is added, radicals can be captured, and the formation of the hydroperoxides is slowed down.

The result of these tests is shown in FIG. 1 in which the time dependence of the increase of oxidized linoleic acid at different concentrations of the antioxidants bilirubin or NCC-1 is plotted.

Our tests have clearly shown (cf. FIG. 1; the concentration of linoleic acid in µM is plotted against time in minutes, the functions without antioxidants are shown, with 20, 100 and 200 µM NCC-1 and 50 µM bilirubin) that the chlorophyll catabolite NCC-1 acts as an antioxidant just like bilirubin. As FIG. 1 shows, a 200 µM addition of NCC-1 is comparable with a 50 µM addition of bilirubin. Without this addition of 200 µM NCC-1 or 50 µM bilirubin the oxidation of linoleic acid is approximately four times faster (topmost curve).

Detailed Experimental Description of the Antioxidant Action of NCC-1:

The action as antioxidant of the non-fluorescent chlorophyll catabolite NCC-1 was investigated by means of the autooxidation reaction of linoleic acid, using azobisisobutyronitrile as radical former. NCC-1 inhibits the oxidation of this fatty acid (approximately by a factor of 4 at a concentration of 200 µm and at room temperature). In these standardized models, the antioxidative action of NCC-1 is approximately comparable with that of the naturally occurring antioxidant bilirubin.

Materials: the solvents for the extraction steps were "reagent-grade" and were distilled before use. The methanol came from Merck Darmstadt, Germany and Acros Organics, Geel, Belgium and was of HPLC grade. 99% bilirubin and 99% linoleic acid were likewise obtained from Acros Organics, aluminum oxide (basic) for chromatography, chloroform puriss. p.a., potassium dihydrogenphosphate puriss. p.a. and dibasically anhydrous potassium phosphate puriss. p.a. came from Fluka, Buchs, Switzerland. Sep-Pak-C18 cartridges came from Waters Associates. The pH measurements were carried out with a WTW Sentix 21 electrode connected to a WTW pH535 digital pH meter.

HPLC: Gynotek HPLC system with manual sampling device, M480 pump (analytical), M300 pump (preparative), Phenomenex DG-301 online degasser, UVD 340 diode array detector and Jasco FP-920 fluorescence detector. The data were collected by means of Gynkosoft 5.50 and processed with Chromelion V6.50. HP 1100 system with manual sampling, online degasser and diode array detector. The data were collected and processed with HP Chemstation for 3D. LC Packings Ultimate Nano-HPLC system with Dionex UVD 340S diode array detector for the LC-MS experiments. The data were collected and processed with Chromelion V6.50.

Analytical HPLC: Hypersil ODS 5 µm 250×4.6 mm-diameter column at room temperature protected by a Phenomenex ODS 4 mm×3 mm-diameter precolumn, flow rate 0.5 mm per minute, 20 µl injection volume. Solvent A: 100 mM potassium phosphate buffer (pH 7.0), solvent B: methanol. Preparative HPLC: Hypersil ODS 5 µm 250 mm×21.2 mm-diameter column at room temperature, flow rate 5 mm per minute; the solvents were degassed through an ultrasound bath, Nano-HPLC: Nucleosil 125-5 50 mm×100 µm-diameter capillary column at room temperature, flow rate 300 µl per minute, 1 µl injection volume. Solvent A: water, solvent B: methanol.

UV/Vis: Hitachi U-3000 spectrophotometer; $\lambda_{max}$(nm)/(rel.∈).

NMR: Varian Unityplus 500 MHz; δ(H) in ppm referenced to δ ($C^1HD_2OD$)=3.31 ppm, coupling coefficients J in Hz; the spectra were recorded at 26° C.

MS: Finigan MAT 95-S in positive-ion mode; FAB-MS with cesium source; 20 keV, glycerol as matrix; ESI-MS: Picoview Nanosource, flow rate 300 µl per minute, spray voltage 1.2 kV, solvent water/methanol 1:2 (v/v).

Determination of the action of NCC-1 as an antioxidant (according to R. Stocker, Y. Yamamoto, A. F. McDonagh, A. N. Glazer, B. N. Arnes, Science 235, 1043 (1987)). Stock solutions of linoleic acid, azobisisobutyronitrile (AIBN), NCC-1 and bilirubin were prepared by dissolving 470 µl linoleic acid in 1530 µl chloroform, 6.9 mg AIBN in 2030 µl chloroform, 0.5 mg NCC-1 in 300 µl chloroform and 0.4 mg bilirubin in 550 µl chloroform. The precise concentrations of NCC-1 and bilirubin in the stock solutions were measured by means of UV/Vis spectroscopy (50 µl of the stock solution was diluted with 3 ml methanol; ∈ (NCC) in methanol at 310 nm is 15000; ∈ (bilirubin) in methanol at 450 nm is 55000). The reaction solutions were prepared by mixing aliquots of the stock solutions at the following concentrations: 0.15 M linoleic acid, 2 mM AIBN and 0-200 µM NCC-1 or bilirubin. The reaction solutions were kept at 37° C., the formation of linoleic acid hydroperoxide was determined by means of UV/Vis spectroscopy or HPLC analysis.

UV/Vis spectroscopy: 40 µl of the reaction mixture was diluted with 3 ml chloroform. The absorption was measured against methanol in the wavelength range 200-800 nm, the total absorption at 234 nm was used to determine the course of the reaction.

Analytical HPLC was carried out at room temperature on a 250 mm×4.6 mm-diameter Hypersil ODS 5 µm column.

The eluant for the isocratic separation was methanol with a flow rate of 1 ml per minute. 40 µl of the reaction mixture was diluted with 1.5 ml chloroform, 20 µl of this solution was applied to the HPLC.

Further advantages of the invention are shown below:

- NCCs are colorless and odorless naturally occurring substances, they are a component of our food in trace amounts.
- NCCs have an antioxidative action comparable with that of bilirubin. But unlike bilirubin (jaundice) NCCs are not known to have any damaging properties.
- plants offer an almost inexhaustible source of these substances; extraction or purification is relatively simple if the right plant type is chosen.
- chlorophyll catabolites cover a very large solubility spectrum, and could therefore be almost universally used, i.e. both in aqueous, i.e. polar, systems and in fatty, i.e. apolar, solvents.
- chemical modifications to NCCs are possible, whereby the spectrum of solubility and polarity properties is naturally also broadened.

they could be used wherever the life of oxidation-sensitive natural products and derivatives thereof should be made longer.

During the development of the novel process, importance was attached primarily to the following points:
  (i) choice of simple and easily upscalable methods (above all no preparative TLC and no preparative HPLC).
  (ii) rapid isolation and preparation in view of the lesser sensitivity of the substance in purified form (enzymes or foreign substances from the plants contained in the plant extract can accelerate the destruction and oxidation of NCCs).
  (iii) suppression of the formation of colored decomposition products during preparation (e.g. by cooling during particular work steps).
  (iv) fine crystallization as last purification step and thus a guarantee of the highest purity and improved storage properties of the oxidation-sensitive substance labile in itself.

Thanks to the properties of NCCs as antioxidant, a further aspect of the invention is a preparation containing at least one compound of formula I

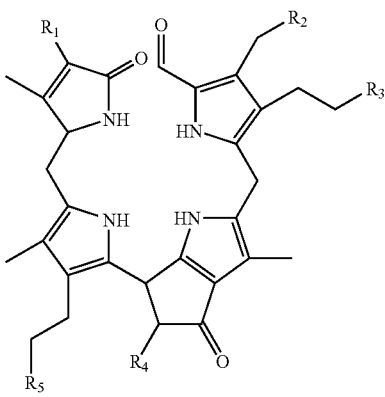

or a pharmacologically, dermatologically or cosmetically acceptable salt or derivative thereof, wherein $R_1$ to $R_5$ is selected from the radicals $R_1$-alkyl, -vinyl, —CHOH—CH$_2$OH
  $R_2$—H, —OH, —Oalkyl, —Oacyl, saccharide radicals, modified saccharide radicals (e.g. malonylated)
  $R_3$—H, —OH, —Oalkyl, —Oacyl, modified —Oacyl (e.g. malonylated), saccharide radicals, modified saccharide radicals (e.g. malonylated)
  $R_4$, $R_5$—COOH, carboxylic acid ester It was shown in further tests that compounds of formula I or NCCs can be used pharmacologically, dermatologically or cosmetically.

It is particularly favorable if $R_1$=vinyl (—CH=CH$_2$) or —CHOH—CH$_2$OH, $R_2$=—H or —OH, $R_3$=—H or —OH or a saccharide radical and $R_4$ or $R_5$=—COOH or —COOCH$_3$.

It is furthermore provided that the preparation contains at least one compound of formula I in a quantity greater than 0.001%.

Such a preparation, in particular for the protection of cells against oxidative stress in order to delay or reduce membrane oxidation, is particularly favorable when it contains one or more antioxidants and/or vitamins, preferably selected from vitamin A palmitate, vitamin C and its derivatives, tocopherol, tocopherol acetate, nicotinic acid, pantothenic acid and biotin. For example, it would be conceivable to prepare a vitamin preparation, e.g. in the form of a capsule or a beverage.

In a further preferred embodiment variant, it is provided that the preparation contains one or more UV filters. In this case it would be advantageous for the preparation to be a cosmetic agent, preferably a skin cream or a sunscreen.

Further studies showed that the compound of formula I has physiological actions. It is therefore favorable for the preparation to be a medicinal product, in particular a medicinal product suitable for prophylaxis and/or treatment in organ transplants or heart attacks.

In this case, it would also be conceivable for the preparation to be a skin treatment agent. For both the creation of a skin treatment agent or a skin cream or sunscreen, it is provided that the preparation contains a hypoallergenic carrier and/or one or more active ingredients with a skincare and/or anti-inflammatory action. Among other things, the excellent UV-absorption properties of NCCs make them particularly suitable as a care/sunscreen agent, skin cream or medicinal product for treating skin diseases. Harmful UV-A and UV-B radiation is thereby transformed into harmless heat radiation.

It is favorable for a preparation as medicinal product to be present in a galenic form, preferably as a cream, capsule, gel, or tablet.

It is furthermore provided that the preparation contains one or more further antioxidants. The combination of several antioxidants improves the antioxidative action overall and has the synergy effect that, in situations in which one antioxidant is not effective, the antioxidative action of the second antioxidant additionally "sets in".

It is furthermore provided that the preparation is a food supplement, preferably in a vitamin preparation.

Due to the excellent properties not only as antioxidant but also the very good membrane permeability, as NCCs are readily soluble both in aqueous solvents and organic solvents, it is particularly suitable for such a preparation to be a preservative, preferably a food preservative.

A further aspect of the invention is the use of the named preparations as preservatives, as medicinal products, as food supplements, as dermatological agents, preferably as sunscreens or skin creams etc.

In a further aspect, the invention relates, due to the excellent properties, to the following points:

Compound of formula I

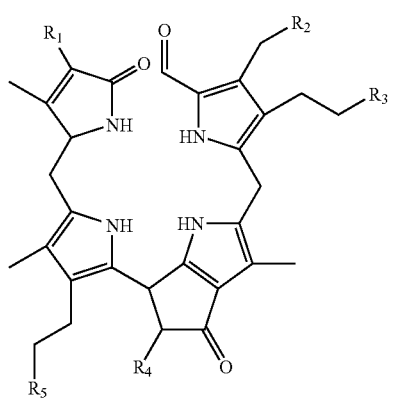

or a pharmacologically, dermatologically or cosmetically acceptable salt or derivative thereof, wherein $R_1$ to $R_5$ is selected from the radicals R₁-alkyl, -vinyl, —CHOH—CH₂OH
R₂—H, —OH, —Oalkyl, —Oacyl, saccharide radicals, modified saccharide radicals (e.g. malonylated)
R₃—H, —OH, —Oalkyl, —Oacyl, modified —Oacyl (e.g. malonylated), saccharide radicals, modified saccharide radicals (e.g. malonylated)
R₄, R₅—COOH, carboxylic acid ester as a preservative, preferably as a food preservative;
for use as a medicinal product;
as an antibacterial;
as a fungicide;
as a food supplement.

It can be assumed on the basis of what is known to date that NCCs can perform a wealth of these and also other functions.

The use of a compound of formula I for the production of a cosmetic preparation, a pharmaceutical preparation, a foodstuff and/or a food supplement is thus provided within the framework of the invention. In this case it is provided to use the compound for protection against oxidative stress and to combat allergies, inflammations and/or irritations, mainly skin irritations.

Specific physiological properties of chlorophyll catabolites, in particular in connection with cancer cells, are explained below. It was shown that NCCs can cause a cell cycle blockade and apoptosis of human cancer cells. Three human tumor cell lines of various organs were used, namely colon cancer cells of the SW480 line, breast cancer cells of the MDAMB231 line and T-cells, leukemia cells of the CCRF-CEM line.

Colorectal cancer (CRC) is the third most common malignoma. The annual incidence of CRC in North America and Europe is approx. 30-50/100,000 inhabitants. In 2000, the American Cancer Society estimated that there were approx. 145,000 new cases and approx. 56,000 deaths due to CRC in the United States of America. In both women and men, CRC is the third most common case of death in each case behind lung cancer and breast cancer or lung and prostate cancer. The average risk of suffering from CRC is approximately 6% over a lifetime.

Uncontrolled cell proliferation is a characteristic of all types of cancer, and a blockade of the cell cycle is therefore regarded as the most efficient strategy for eliminating cancer cells. Various cell cycle inhibitors are currently known which are used to treat cancer in preclinical and clinical studies. The cell cycle in eukaryotes is at least partly controlled by a family of protein kinase complexes, wherein each of these complexes consists of a catalytic sub-unit, the so-called cyclin-dependent-kinase (CDK), and its essential regulatory sub-unit, cyclin. These complexes are activated at specific times during each cell cycle. But they can also be regulated by exogenous factors. The cyclin-CDK complex can be inhibited by binding of a specific class of proteins, known as cyclin-kinase inhibitors (CKI). Anticarcinogens can influence one or more of the regulatory steps in the cell cycle, which leads to a blockade of the cell cycle progression, whereby the growth and proliferation of the cancer cells is reduced. A cell cycle blockade can lead to a programmed cell death (i.e. to the apoptosis of the cancer cell). The property of tumor cells to avoid apoptosis is an important feature of resistance to conventional treatments.

It was shown in the present study that NCC-1 effects a disruption of the cell cycle and an induction of apoptosis in various human cancer cells.

Materials and Methods Used;

Reagents: the more than 95% pure chlorophyll catabolite NCC-1 was obtained according to the previously described purification process from the senescent leaves of *Cercidiphyllum japonicum*. A stock solution of NCC-1 was dissolved by dissolving 0.5 g with 70 mg KH₂PO₄ in a minimal quantity of Dulbeccos PPS buffer (obtained from PAA Laboratories GmbH, Pasching, Austria). Annexin-V APC and propidium iodide, Annexin-V Fitc and 7-AAD dye solution were obtained from BD Farmingen (Heidelberg, Germany) and Sigma Aldrich (Germany).

Cell culture: the human colon carcinoma cell line SW480 came from the German Collection of Microorganisms and Cell Cultures (Braunschweig, Germany). MDAMB231 and CCRF-CEM came from the American Type Culture Collection (Rockville, Md.). The SW480 cells were cultured in Dulbeccos modified Eagles-Medium (DMEM; Sigma Alrich Chemie, Steinheim, Germany); MDAMB231 cells were cultured in MEM (PAA Laboratories GmbH Pasching, Austria). CCRF-CEM cultures were cultured in RPMI 1640 (PAA Laboratories). 2 mM L-glutamine, 10% FCS (fetal calf serum) and 1% penicillin-streptomycin were added to all media. The cells were kept in a moist environment under stand cell culture conditions at 37° C. and 5% CO₂.

Treatment of cells: The stock solution of NCC-1 was filtered through a 0.22-μm filter (Millex®-GS, Millipor, Carrigtwohill, Co. Cork, Ireland) into a sterile flask and diluted with the cell culture medium. The final NCC-1 concentration was between 50 μM and 200 μM. SW480 and MDAMB231 were cultured to 70 to 80% confluence in "6-well plates" (BD Biosciences) and were then treated with NCC-1 (1,000, 800, 600, 400, 200 μM/L medium) for 24, 48 and 72 hours in complete cell culture medium. CCRF-CEM (300,000 cells/ml) were treated with NCC-1 (800, 400, 200, 100 and 50 μM/L medium).

³H-thymidine incorporation tests: MDAMB231 cells (10,000 cells/well) were introduced into flat-bottomed "96-well microtiter plates" in 200 μl growth medium with 5% FCS and these were cultured with media at various NCC-1 concentrations (800, 1,200, 1,600, 2,000 μM/L) or medium alone. These cells were cultured for 18 hours with NCC-1. 1 μCi of ³H-thymidine was then added, followed by an incubation at 37° C. in a moist 5% CO₂ atmosphere for a further six hours; this was then stored overnight at −70° C. On the following day, the frozen plate was thawed at 37° C. and the incorporation of ³H-thymidine established by liquid scintillation measurement. Each sample was measured four times.

Determination of apoptosis by means of throughflow cytometry: CCRF-CEM was cultured in 6-well plates (300,000 cells/ml) and treated with NCC-1 (800, 400, 200, 100 and 50 μM/L) for 24 hours, 48 hours and 72 hours. The cells were rinsed twice with cold PBS and resuspended in the binding buffer (1 mM Hepes/NaOH, pH 7.4, 140 mM NaCl, 2.5 mM CaCl₂). 5 μl Annexin-V-FITC (BD Farmingen) and 5 μl 7-amino-actinomycin D (7-ADD, BD Farmingen) were added and incubated for 15 minutes at room temperature with the exclusion of light.

DNA cell cycle analysis: adherent cells (SW480 and MDAMB231; 70 to 80% confluent) were treated with NCC-1 (1,000, 800, 600, 400, 200 μM/L). The suspended cells CCRF-CEM were treated in 800, 400, 200, 100 and 50 μM NCC-1/L in complete medium for 24, 48, and 72 hours. SW480 and MDAMB231 were then digested twice with trypsin, washed twice with cold PBS and centrifuged. CCRF-CEM cells were washed twice with cold PBS and centrifuged. The cell pellet was resuspended in 50 μl Nicoletti buffer (the final propidium iodide concentration was 50 μg/ml), then incubated for two hours at 4° C. in the dark and finally analyzed by means of throughflow cytometry.

Preparation of Cell Lysates and Western Blot Analysis: the CCRF-CEM Cells were harvested after 4, 8, 24 and 48 hours in each case after NCC-1 treatment (200 µm; as described above) and washed with cold PBS. The cells were incubated in ice-cooled lysis buffer (50 mM/L Tris-HCl, 100 mM/L NaCl, 50 mM/L NaF, 5 mM/L EDTA, 40 mM β-glycerophosphate, 1% Triton X-100) and fresh Halt Protease Inhibitor Cocktail (Pierce, Ill., USA) and 200 µM/L $Na_3VO_4$ added. The cells were lysed during several freezing and thawing cycles (alternating cooling by means of liquid nitrogen and heating to 37° C.). The lysate was cleaned by centrifuging at 14,000 g for 15 minutes at 4° C., the residue (the whole cell lysate) was collected, aliquoted and stored at −70° C. The protein content of the lysates was analyzed by Bio-Rad Protein Assay (Bio-Rad Laboratories) in accordance with the manufacturer's directions.

For the Western blot analysis, 50 µg protein was dissolved on 8 to 12% SDS-PAGE gel and transferred onto a nitrocellulose membrane. The non-specific points were blocked by incubating the blot with 5% fat-free dried milk in buffer (containing 10 mM/L Tris, 100 mM/L NaCl, 0.1% Tween 20) for one hour at room temperature or overnight at 4° C. The blot was then washed three times with washing buffer (10 mM/L Tris, 100 mM/L NaCl, 0.1% Tween 20) for ten minutes each time and the incubation then took place overnight with a suitable primary antibody specific to the protein to be determined. The antibodies were used in concentrations named by the manufacturer. The blot was washed twice for 20 minutes each time, followed by incubation with the corresponding secondary antibody, which is horse-radish peroxidase (HRPO) conjugated (Amersham Life Science Inc., Arlington Heights, Ill.) at a 1:2,000 dilution for one hour at room temperature. The blot was then washed twice in washing buffer for ten minutes each time and four times for five minutes each time. The protein content was detected by means of chemiluminescence with the Enhanced Chemiluminescence Kit (Amersham Life Science) and autoradiography with XAR-5-Film (Amersham Life Science). For each immunoblot, the same protein content was confirmed by "stripping" the blot and re-investigating with β-actin antibodies.

The findings and results of the cancer-therapy action of NCC-1 are described with the help of FIGS. 2 to 6 and the description of the figures. Three human cell lines of various organs were used, namely colon cancer cells of the SW480 line, breast cancer cells of the MDAMB231 line and T-cells, leukemia cells of the CCRF-CEM line.

In the first part of the experiments, it was investigated whether NCC-1 treatment of the cell lines has an anti-proliferative effect on the cancer cells. For this purpose, the in-vitro effect of NCC-1 on the tumor cell proliferation was investigated by means of tritium thymidine incorporation assay. It was shown that NCC-1 treatment of three different cancer cell lines resulted in a dose-related reduction of the growth of all cell types (see FIG. 2; the data for SW 480 and CCRF-CEM are not shown, for clarity's sake; the diagram shows the % cell growth in relation to the NCC-1 concentration: control=0, 800, 1,200, 1,600, 2,000 µM). As the dose is increased, a reduction to ca. 15% compared with a control with a relative cell growth of 100% was achieved with a 2,000 µM/L NCC-1 treatment. The bars represent the average of three different experiments; the standard deviation is illustrated by means of error bar lines.

In a next step, the influence of NCC-1 on the cell cycle of cancer cells was investigated (FIGS. 3A to 3C; the percentage of dead cells is plotted against the NCC-1 concentration, the 3 columns stand for 24, 48 and 72 hours). The growing cells were treated with NCC-1 for 24, 48 and 72 hours, the DNA cell cycle was analyzed as previously described. It was shown that, compared with a control, with the addition of NCC-1 the number of dead cells (in percent) increased considerably compared with the control. FIG. 3A shows the experiment for MDAMB231 cells, in FIG. 3B that for SW480 cells and in FIG. 3C that for CCRF-CEM cells. The columns show the average of three different experiments, in duplicates in each case, wherein the standard deviation is also shown.

As was shown in FIGS. 3A to 3C, NCC-1 induces cell death in different cancer cell types. Microscope studies showed different cell morphologies for different concentrations of NCC. At low concentrations, the NCC-1 treatment of the cancer cells caused blistering on the cells, which is a typical sign of apoptosis, while the cells swelled at higher NCC-1 concentration treatments, which is an indication of necrosis. As a result of these preliminary tests, it was then investigated whether the various morphological differences corresponded to different types of cell death.

Apoptotic cell death is the result of a series of precisely regulated events which are often modified in tumor cells. This offers a possibility of selective clinical intervention in order to induce a programmed cell death of the cancer cells, ideally without influencing the normal cells. Apoptosis is a physiological process which involves the elimination of cells with DNA damage and it represents a separate form of cell death which differs from necrotic cell death. Consequently, substances which can regulate or influence apoptosis can be used in cancer therapy.

As shown in FIG. 4 (the percentage of Annexin-V-positive cells are plotted against the NCC-1 concentration, the three columns stand for 24, 48, 72 hours), for CCRF-CEM cells treatment with NCC-1 results in a dose-related induction of apoptosis. Compared with the controls, an almost 100% Annexin-V-positive result was achieved when 400 µM NCC-1 or more was added.

It was shown in cell cytometry analyses (FACS) that in all three cell lines a dose-related G2 arrest takes place as a result of NCC-1 treatment (FIGS. 5A-5F; the growing cells were treated both with pure cell culture medium for 24 hours (5A), 48 hours (5B) and 72 hours (5C) and with 100 µM NCC-1 for 24 hours (5D), 48 hours (5E) and 72 hours (5F)). This is an indication that the induction of apoptosis is dependent on the cell cycle. To test these indications, it was confirmed in a further series of experiments that the apoptosis of the CCRF-CEM cells due to NCC-1 is caused by a cell cycle blockade. This investigation is particularly important, as molecular analyses of human cancer have shown that cell cycle regulators are often mutated in malignant diseases. In FIGS. 5A to 5F the effect of the NCC-1 treatment on the cell cycle in the CCRF-CEM cells is shown. The growing cells were treated in medium alone for 24 hours (A), 48 hours (B) and 72 hours (C) or with NCC-1 (100 µmol/L) for 24 hours (D), 48 hours (E) and 72 hours (F). In the figures, the number is represented as a function of size. A shift towards different sizes is clearly recognizable.

In a next step, the influence of NCC-1 on the CKI-cyclin-CDK machinery in G2/M phase cell cycle arrest in human cancer cells was investigated. The progression of the cells through the cell cycles in eukaryotes is coordinated by the above-mentioned family of protein kinase complexes. Each complex is, as already mentioned, composed at least of the regulatory sub-unit cyclin, which binds to the catalytic CDK sub-unit in order to form the active cyclin-CDK complex. Such complexes are activated at different times after specific intervals during the cell cycle and can also be regulated by exogenous factors. In transformed cells, the cell progression is a mitogenic process dependent or not on the signal. CDK activity is also regulated by small proteins, known as CKIs. CKIs contain the p21/WAF1 and p27/KIP1 protein families.

The modeling in cell cycle regulatory events was thus investigated in connection with the G2/M phase as a mechanism of NCC-1-induced cell cycle disruption and apoptosis in human CCRF-CEM cells.

It was shown by means of Western-blot analysis (FIG. 6) for the NCC-1 treatment (200 μMol/L for 4, 8 and 24 hours, control was cultured with medium alone) of CCRF-CEM cells that a significant upward adjustment of the CKI p27/KIP1 protein took place. In earlier studies, the critical role of p27/KIP1 in apoptosis and cell cycle progression was shown by the G2 phase.

The shown experimental data furnish sound proof that NCCs have a therapeutic action in the case of cancers and have a preventative effect against such diseases. A targeted addition of NCCs to dermatological products and foodstuffs can therefore have a preventative function for certain diseases in addition to having a preservative effect.

The invention claimed is:

1. A preparation comprising:
   at least one compound of formula I

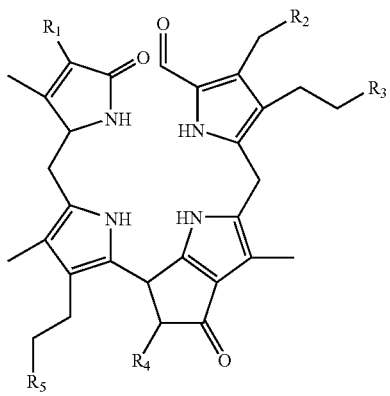

or a pharmacologically, dermatologically or cosmetically acceptable salt thereof, wherein $R_1$ is -alkyl, -vinyl, or —CHOH—CH$_2$OH; $R_2$ is —H, —OH, —O-alkyl, —O-acyl, saccharide radicals, or modified saccharide radicals; $R_3$ is —H, —OH, —O-alkyl, —O-acyl, modified —O-acyl, saccharide radicals, or modified saccharide radicals; $R_4$ is —COOH or a carboxylic acid ester; and $R_5$ is —COOH or a carboxylic acid ester; and
   at least one substance selected from the group consisting of an antioxidant and a vitamin.

2. The preparation according to claim 1, wherein $R_1$ is —CH=CH$_2$ or —CHOH—CH$_2$OH, $R_2$ is —H or —OH, $R_3$ is —H, —OH or a saccharide radical, $R_4$ is —H or CH$_3$ and $R_5$ is —COOH.

3. The preparation according to claim 1, wherein the preparation comprises at least one compound of formula I in a quantity greater than 0.001%.

4. The preparation according to claim 1, wherein the at least one substance is selected from the group consisting of vitamin A, vitamin A palmitate, vitamin C and its-derivatives compounds, tocopherol, tocopherol acetate, nicotinic acid, pantothenic acid, biotin, and mixtures thereof.

5. The preparation according to claim 1, wherein the preparation further comprises one or more UV filters.

6. A cosmetic agent comprising the preparation according to claim 1.

7. A medicinal product comprising the preparation according to claim 1.

8. A skin treatment agent comprising the preparation according to claim 1.

9. The preparation according to claim 1, further comprising at least one substance selected from the group consisting of a hypoallergenic support, skincare active ingredients and anti-inflammatory agents.

10. The medicinal product according to claim 7, which is in a galenic form.

11. A food supplement comprising the preparation according to claim 1.

12. A preservative comprising the preparation according to claim 1.

13. An antioxidant comprising the preparation according to claim 1.

14. A dermatological agent comprising the preparation according to claim 1.

15. A method of using a compound of formula I

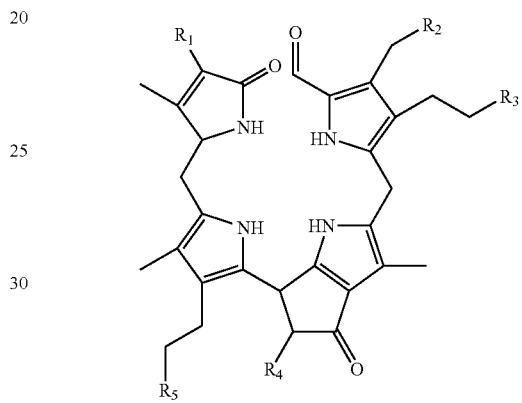

or a pharmacologically, dermatologically or cosmetically acceptable salt thereof, wherein $R_1$ is -alkyl, -vinyl, or —CHOH—CH$_2$OH; $R_2$ is —H, —OH, —O-alkyl, —O-acyl, saccharide radicals, or modified saccharide radicals; $R_3$ is —H, —OH, —O-alkyl, —O-acyl, modified —O-acyl, saccharide radicals, or modified saccharide radicals; $R_4$ is —COOH or a carboxylic acid ester; and $R_5$ is —COOH or a carboxylic acid ester, as a preservative,
   said method comprising contacting the compound, pharmacologically, dermatologically or cosmetically acceptable salt thereof with an article to be preserved.

16. A method of using a compound of formula I

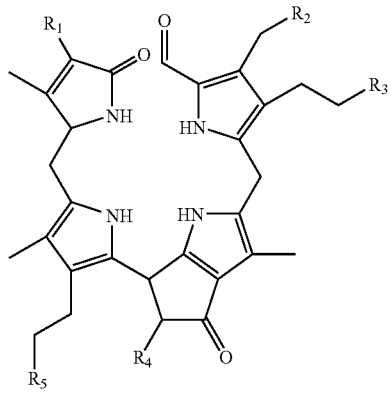

or a pharmacologically, dermatologically or cosmetically acceptable salt thereof, wherein $R_1$ is -alkyl, -vinyl, or —CHOH—CH$_2$OH; R$_2$ is —H, —OH, —O-alkyl, —O-acyl, saccharide radicals, or modified saccharide radicals; R$_3$ is —H, —OH, —O-alkyl, —O-acyl, modified —O-acyl, saccharide radicals, or modified saccharide radicals; R$_4$ is —COOH or a carboxylic acid ester; and R$_5$ is —COOH or a carboxylic acid ester, as an antibacterial agent, said method comprising contacting the compound, pharmacologically, dermatologically or cosmetically acceptable salt thereof with bacteria.

17. A method of using a compound formula I

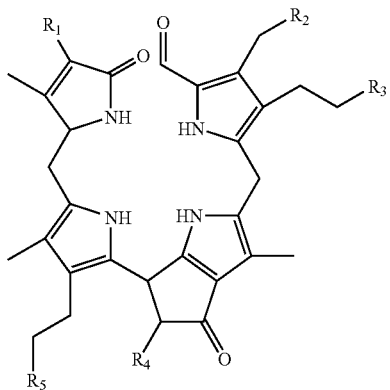

or a pharmacologically, dermatologically or cosmetically acceptable salt thereof, wherein R$_1$ is -alkyl, -vinyl, or —CHOH—CH$_2$OH; R$_2$ is —H, —OH, —O-alkyl, —O-acyl, saccharide radicals, or modified saccharide radicals; R$_3$ is —H, —OH, —O-alkyl, —O-acyl, modified —O-acyl, saccharide radicals, or modified saccharide radicals; R$_4$ is —COOH or a carboxylic acid ester; and R$_5$ is —COOH or a carboxylic acid ester, as a fungicide, said method comprising contacting the compound, pharmacologically, dermatologically or cosmetically acceptable salt thereof with a fungus.

18. A method of using a compound of formula I

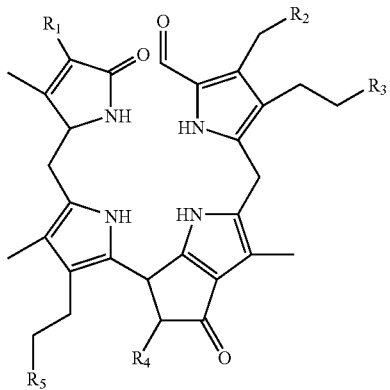

or a pharmacologically, dermatologically or cosmetically acceptable salt thereof, wherein R$_1$ is -alkyl, -vinyl, or —CHOH—CH$_2$OH; R$_2$ is —H, —OH, —O-alkyl, —O-acyl, saccharide radicals, or modified saccharide radicals; R$_3$ is —H, —OH, —O-alkyl, —O-acyl, modified —O-acyl, saccharide radicals, or modified saccharide radicals; R$_4$ is —COON or a carboxylic acid ester; and R$_5$ is —COON or a carboxylic acid ester, as a food supplement, said method comprising supplementing the compound, pharmacologically, dermatologically or cosmetically acceptable salt thereof for food.

19. A method of treating carcinoma, comprising administering a therapeutically effective amount of a compound of formula I

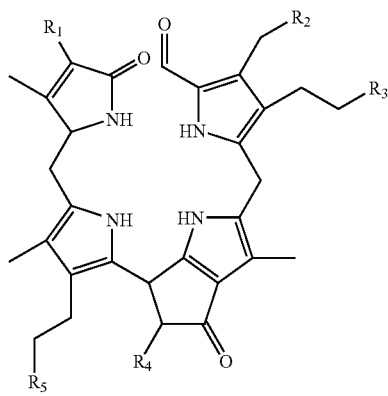

or a pharmacologically, dermatologically or cosmetically acceptable salt thereof, wherein R$_1$ is -alkyl, -vinyl, or —CHOH—CH$_2$OH; R$_2$ is —H, —OH, —O-alkyl, —O-acyl, saccharide radicals, or modified saccharide radicals; R$_3$ is —H, —OH, —O-alkyl, —O-acyl, modified —O-acyl, saccharide radicals, or modified saccharide radicals; R$_4$ is —COOH or a carboxylic acid ester; and R$_5$ is —COOH or a carboxylic acid ester, to a patient in need thereof.

20. A method of preparing a cosmetic preparation, a pharmaceutical preparation, a foodstuff or a food supplement, said method comprising contacting a compound of formula I

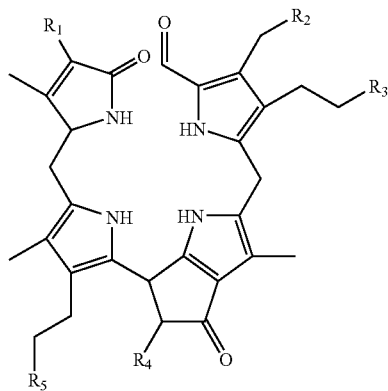

or a pharmacologically, dermatologically or cosmetically acceptable salt thereof, wherein R$_1$ is -alkyl, -vinyl, or —CHOH—CH$_2$OH; R$_2$ is —H, —OH, —O-alkyl, —O-acyl, saccharide radicals, or modified saccharide radicals; R$_3$ is —H, —OH, —O-alkyl, —O-acyl, modified —O-acyl, saccharide radicals, or modified saccharide radicals; R$_4$ is —COOH or a carboxylic acid ester; and R$_5$ is —COOH or a carboxylic acid ester, with a cosmetic, a pharmaceutical, a foodstuff or a food supplement.

21. A process for producing non-fluorescent chlorophyll catabolites of formula I

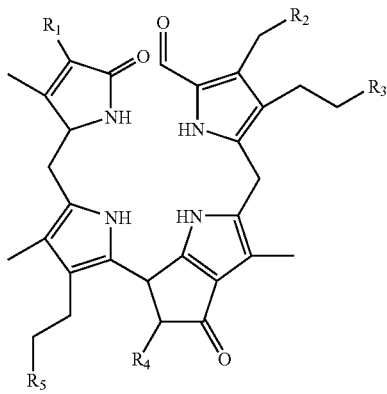

or a pharmacologically, dermatologically or cosmetically acceptable salt thereof, or a plant salt thereof,
wherein $R_1$ is -alkyl, -vinyl, or —CHOH—CH$_2$OH; $R_2$ is —H, —OH, —O-alkyl, —O-acyl, saccharide radicals, or modified saccharide radicals; $R_3$ is —H, —OH, —O-alkyl, —O-acyl, modified —O-acyl, saccharide radicals, or modified saccharide radicals; $R_4$ is —COOH or a carboxylic acid ester; and $R_5$ is —COOH or a carboxylic acid ester,
from a plant material,
said method comprising the steps:
extraction of the plant material with a first solvent or solvent mixture with a dielectric constant of 5 to 20 and a dipole moment of 5 to $10 \times 10^{-30}$ cm to form a crude extract
filtration by column chromatography of this extract over silica gel
elution of the silica gel with a second solvent or solvent mixture, and
drawing off of the solvent to obtain a residue, and optional crystallization of the obtained residue.

22. The process according to claim 21, wherein the first solvent is CH$_2$Cl$_2$, methyl acetate, ethyl acetate, t-butanol, ethyl methyl ketone or mixtures thereof.

23. The process according to claim 21, wherein the filtration step is carried out with a silica-gel-filled chromatography column.

24. The process according to claim 21, wherein a solvent of greater polarity than the first solvent is used as solvent for the elution step and the solvent is selected from the group consisting of acetone, ethyl methyl ketone, methanol, methanol-water mixtures, methyl acetate, mixtures thereof and mixtures of the first solvent or solvent mixture with a solvent of greater polarity.

25. The process according to claim 21, comprising a purification step of the crude extract with a non-miscible solvent or a non-miscible aqueous solution before the filtration step.

26. The process according to claim 21, wherein the eluate is washed with an aqueous solution.

27. The process according to claim 21, wherein the residue is crystallized, and then filtered and dried.

28. The process according to claim 21, wherein the silica gel has a particle size of less than 5,000.

29. The process according to claim 21, wherein the plant material is plant parts which are green before ripening or senescence or contain chlorophylls.

30. The process according to claim 21, wherein the plant material is substantially senescent or ripened plant material.

31. The process according to claim 21, wherein the plant material is freshly harvested, senescent or ripened plant material, or senescent or ripened plant material which has been stored frozen after harvest at approximately –20° C. or below.

32. The process according to claim 21, wherein the plant material comes from agricultural plants, herbaceous plants, agriculturally produced vegetables, shrubs, broad-leaved trees and conifers.

33. The process according to claim 1, wherein the modified saccharide radicals and/or the modified O-acyl groups are malonylated.

34. The preparation according to claim 1, wherein the preparation comprises at least one compound of formula I in a quantity greater than 0.1%.

35. A method of protecting against oxidative stress and combating allergies, inflammations or irritations,
said method comprising administering a therapeutically effective amount of a compound of formula I

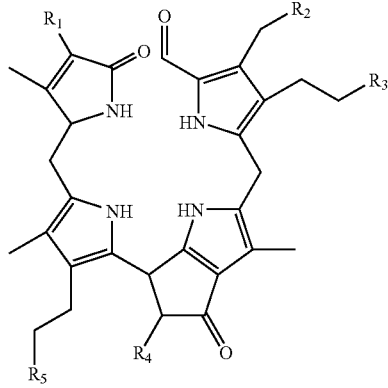

or a pharmacologically, dermatologically or cosmetically acceptable salt thereof, wherein $R_1$ is -alkyl, -vinyl, or —CHOH—CH$_2$OH; $R_2$ is —H, —OH, —O-alkyl, —O-acyl, saccharide radicals, or modified saccharide radicals; $R_3$ is —H, —OH, —O-alkyl, —O-acyl, modified —O-acyl, saccharide radicals, or modified saccharide radicals; $R_4$ is —COOH or a carboxylic acid ester; and $R_5$ is —COOH or a carboxylic acid ester,
to a patient in need thereof.

36. The process according to claim 21, wherein the plant material is plant leaves.

37. The process according to claim 21, wherein the second solvent has a greater polarity than the first solvent.

38. The process according to claim 21, wherein the modified saccharide radicals and/or the modified O-acyl groups are malonylated.

39. The process according to claim 32, wherein the agricultural plant is selected from the group consisting of oil seed rape, clover, barley, corn and tobacco.

40. The process according to claim 32, wherein the agriculturally produced vegetable is selected from the group consisting of spinach, broccoli and pepper.

41. The process according to claim 32, wherein the broad-leaved tree is selected from the group consisting of witch hazel, elm, sycamore, walnut, Cercidiphyllum japonicum.

42. The process according to claim 32, wherein the conifer is a larch.

43. The method according to claim 19, wherein the modified saccharide radicals and/or the modified O-acyl groups are malonylated.

44. The method according to claim 20, wherein the modified saccharide radicals and/or the modified O-acyl groups are malonylated.

* * * * *